(12) United States Patent
Berris

(10) Patent No.: US 8,642,497 B2
(45) Date of Patent: Feb. 4, 2014

(54) PROCESSES FOR THE PREPARATION OF TETRAKIS($^F$ARYL)BORATE SALTS

(75) Inventor: Bruce C. Berris, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 1086 days.

(21) Appl. No.: 12/097,246

(22) PCT Filed: Dec. 8, 2006

(86) PCT No.: PCT/US2006/061805
§ 371 (c)(1),
(2), (4) Date: Jun. 12, 2008

(87) PCT Pub. No.: WO2007/070770
PCT Pub. Date: Jun. 21, 2007

(65) Prior Publication Data
US 2008/0306302 A1    Dec. 11, 2008

Related U.S. Application Data

(60) Provisional application No. 60/749,866, filed on Dec. 12, 2005.

(51) Int. Cl.
*B01J 21/02* (2006.01)
(52) U.S. Cl.
USPC .......................................... 502/202; 502/203
(58) Field of Classification Search
None
See application file for complete search history.

(56) References Cited

U.S. PATENT DOCUMENTS

| | | | |
|---|---|---|---|
| 3,232,947 | A | 2/1966 | Haszeldine et al. |
| 5,679,289 | A | 10/1997 | Krafft |
| 6,580,007 | B1 | 6/2003 | Dury et al. |
| 6,635,597 | B1 | 10/2003 | Marks et al. |
| 6,700,019 | B2 | 3/2004 | Dury et al. |

FOREIGN PATENT DOCUMENTS

| | | |
|---|---|---|
| EP | 1 048 636 A1 | 11/2000 |
| WO | WO 99/06412 A1 | 2/1999 |

OTHER PUBLICATIONS 2003-2004 Aldrich Chemical Catalog (received Sep. 25, 2002) p. 262-263.*
B. Gething, et al; "Polycyclic Fluoroaromatic Compounds. Part I. Some Reactions of Octafluoronaphthalene"; Journal of the Chemical Society; 1962; p. 186-190; Chemical Society; United Kingdom.
Dewey G. Holland, et al; "The Oxidation-Reduction Reaction of Hydrazinofluoro Aromatic Compounds. I. para-Substituted Perfluoro Aromatic Hydrazines"; The Journal of Organic Chemistry; Jun. 1964; vol. 29; p. 3042-3046; American Chemical Society Publications; USA.
Dewey G. Holland, et al; "Preparation and Reactions of Hydrazino Perfluoroaromatic Compounds"; The Journal of Organic Chemistry; Jun. 1964; vol. 29; p. 1562-1565; American Chemical Society Publications; USA.
Christ Tamborski, et al; "Difunctional Tetrafluorobenzene Compounds From Fluoroaromatic Organolithium Intermediates"; The Journal of Organic Chemistry; Mar. 1966; vol. 31; No. 3, p. 746-749; American Chemical Society Publications; USA.
Liting Li, et al; "New Organo-Lewis Acids. Tris(β-perfluoronaphthyl)borane (PNB) As a Highly Active Cocatalyst for Metallocene-Mediated Ziegler-Natta a-Olefin Polymerization"; Organometallics; 1998; vol. 17; p. 3996-4003; American Chemical Society Publications; USA.

* cited by examiner

*Primary Examiner* — Clinton Brooks
(74) *Attorney, Agent, or Firm* — James A. Jubinsky; Nathan C. Dunn; Marcy M. Hoefling

(57) ABSTRACT

A process for the preparation of organic cation tetrakis($^F$aryl) borate salts. The process includes preparation of intermediate, mono-hydrazine substituted ($^F$aryl) compound, from ($^F$aryl) compound using hydrazine at temperatures below 78° C. A stoichiometric excess of hydrazine to the ($^F$aryl) compound to the ($^F$aryl) compound is used. The process further includes the preparation of the organic cation tetrakis($^F$aryl) borate in ethereal medium.

18 Claims, No Drawings

PROCESSES FOR THE PREPARATION OF TETRAKIS($^F$ARYL)BORATE SALTS

FIELD OF THE INVENTION

This invention relates generally to improved processes for the preparation of tetrakis($^F$aryl)borate salts, particularly to the preparation of tetrakis(perfluoronaphthyl)borate salts, and more particularly to the preparation of tetrakis(perfluoronaphthyl)dimethylanilinium borate salts.

BACKGROUND

Various terms are defined in the following specification. For convenience, a Glossary of terms is provided herein, immediately preceding the claims.

Tetrakis(perfluoroaryl)borate derivatives are useful as activators/co-catalysts for metallocenes in processes for polymerization of olefins to polymers. For example, such derivatives are useful in the polymerization of linear copolymers of ethylene. There are many publications related to the preparation of these activators/co-catalysts. See, for example, Li, L. and Marks, T. J., *Organometallics* 1998, 17, 3996-4003; U.S. Pat. No. 6,635,597; U.S. Pat. No. 5,679,289; and U.S. Pat. No. 6,580,007. In particular, Mars, et al., WO 99/06412, describes a modified procedure of Gething, et al., *J. Chem. Soc.* 1962, 36, 186, for making a precursor to the tetrakis (perfluoroaryl)borate, i.e., heptafluoro-2-naphthylhydrazine, from octafluoronaphthalene by reaction with hydrazine hydrate. The process uses stoichiometric quantities of hydrazine and octafluoronaphthlene (OFN) and reacts them together at reflux in ethanol. Various publications list the boiling point of ethanol as about 78° C. The reported procedures for making tetra(perfluoroaryl)borate salts and the related triarylboranes usually involve lithiating the fluorinated precursor in a hydrocarbon solvent, or the use of Grignard reagents in ether solution (see, e.g., U.S. Pat. No. 6,700,019). None of these reported procedures are suitable for making tetrarylborates in high enough yields and with purities that are suitable for commercial use. Furthermore, the lithiation of 2-bromoheptafluoronaphthalene, in pentane solvent, as reported in Li, L, and Marks, T, *J. Organometallics* 1998, 17, 3996-4003, caused the lithium derivative to precipitate. This could present difficulties in the event of the expected exothermic decomposition. Improved processes are thus needed.

SUMMARY OF THE INVENTION

This invention provides improved processes useful in the preparation of tetrakis($^F$aryl)borate salts. In one embodiment, the invention provides processes for the preparation of monohydrazine substituted ($^F$aryl) compounds comprising combining ($^F$aryl) compound and hydrazine at a temperature below about 78° C. An advantage as compared to published processes is that selectivity as to the desired mono-hydrazine substituted ($^F$aryl) compound is improved at temperatures below about 78° C. In another embodiment, the invention provides processes for the preparation of mono-hydrazine substituted ($^F$aryl) compounds comprising combining ($^F$aryl) compound and a stoichiometric excess of hydrazine at a temperature below about 78° C. An advantage is that the stoichiometric excess of hydrazine assists in maintaining a reasonable reaction time as the reaction temperature decreases. In another embodiment, the invention provides processes for the preparation of tetrakis($^F$aryl)borate salts comprising lithiating brominated ($^F$aryl) compound in ether solvent to form first product and treating at least a portion of the first product with boron trichloride. An advantage as compared to published processes that use an aliphatic hydrocarbon solvent is that with use of ether solvent the reaction continues more toward completion. A further advantage of using ether solvent is that ether solvent will dissolve the lithium derivative under most conditions, which lessens the probability of a localized powerful exotherm.

Schematically, the improved processes of this invention can include the following reactions:

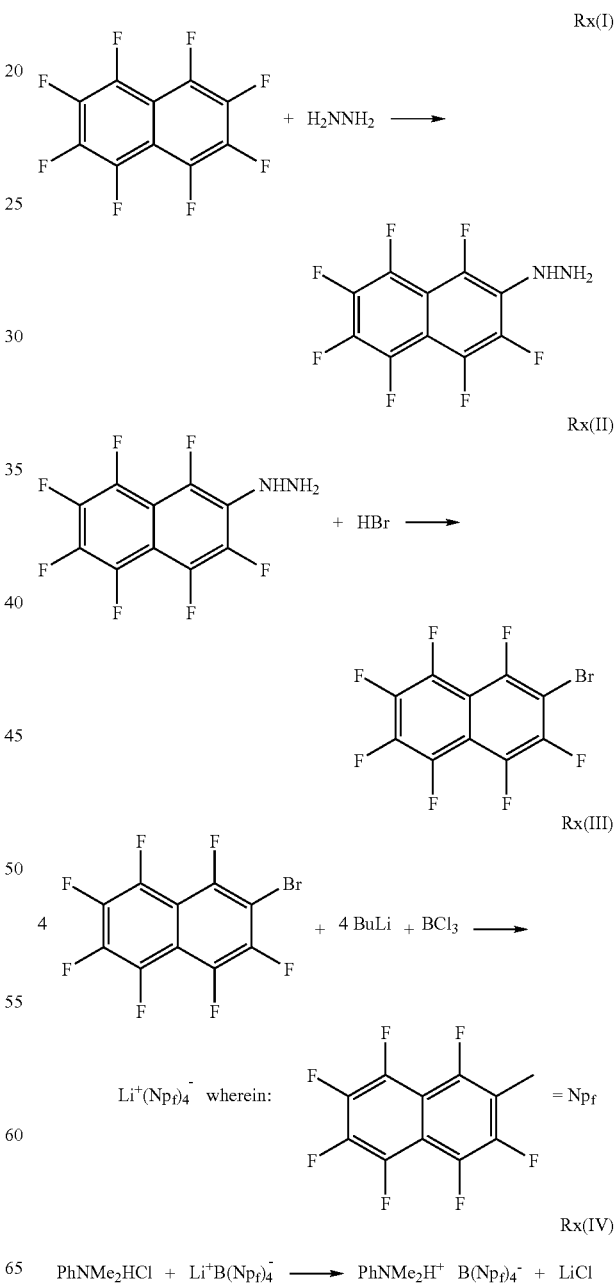

DETAILED DESCRIPTION OF THE INVENTION

The improved processes of this invention will be described in connection with specific embodiments. It is understood that this invention is not limited to any one of these specific embodiments.

In one embodiment of this invention, a process is provided for preparing ($^F$aryl) hydrazine compound comprising combining ($^F$aryl) compound and hydrazine in a solvent below about 78° C. [see, e.g., Rx (I)]. The ($^F$aryl) compound may comprise perfluoroaryl compounds particularly octafluoronapthalene. In certain embodiments, a stoichiometric excess of hydrazine to the ($^F$aryl) compound is used, for example at least about 3 molar equivalents of hydrazine to one molar equivalent of ($^F$aryl) compound is used, or more particularly, about four molar equivalents of hydrazine to one molar equivalent of ($^F$aryl) compound is used.

In one embodiment of this inventions a process is provided for preparing tetrakis($^F$aryl) borate salt. The process comprises: (i) combining brominated ($^F$aryl) compound and alkyllithium in the presence of solvent comprising ether to produce first product, (ii) combining at least a portion of the first product and boron trihalide to produce second product [see, e.g., Rx (III)]; and (iii) isolating tetrakis($^F$aryl) borate salt from the second product. In one embodiment, (iii) comprises combining at least a portion of the second product and second solvent to isolate tetrakis($^F$aryl) borate salt. The tetrakis ($^F$aryl) borate salt may comprise tetrakis(perfluoronaphthyl) borate, tetrakis(perfluoronaphth-2-yl)borate, dimethylanilinium tetrakis(perfluoronaphthyl) borate, or dimethylanilinium tetrakis(perfluoronaphth-2-yl)borate. The brominated ($^F$aryl) compound may comprise 2-bromoheptafluoronaphthalene; the alkyllithium may comprise butyllithium; and/or the boron trihalide may comprise boron trichloride. The second solvent may be halogenated solvent, such as halogenated hydrocarbon, and may comprise methylene chloride. In one embodiment Rx(III) comprises formation of an intermediate LiNp$_f$+BuBr, then LiNp$_f$ reacts with BCl$_3$ to make lithium salt and three LiCl.

In one embodiment of this invention, a process is provided for preparing tetrakis($^F$aryl)borate salt. The process comprises: (i) combining ($^F$aryl) compound and hydrazine in solvent below about 78° C. to form ($^F$aryl)hydrazine; (ii) converting at least a portion of the ($^F$aryl)hydrazine to bromo ($^F$aryl) compound [see e.g., Rx (II)]; (iii) combining at least a portion of the bromo($^F$aryl) compound and alkyllithium in ethereal medium to form reaction mixture, (iv) combining boron trihalide compound and at least a portion of the reaction mixture to form lithium tetrakis($^F$aryl)borate [see, e.g., Rx (III)]; and (v) exchanging lithium cation of at least a portion of the lithium tetrakis($^F$aryl)borate for cation of organic salt to form tetrakis($^F$aryl)borate salt [see, e.g., Rx (IV)]. The boron trihalide compound may comprise boron trifluoride or boron trichloride; and/or the alkyllithium may comprise n-butyllithium, phenyllithium, methyllithium, sec-butyllithium, t-butyllithium; or hexyllithium; and/or the organic salt may comprise triarylmethyl salts, protic ammonium salts, dimethyl anilinium salts, or onium salts. The ethereal medium comprises at least about 50% by volume (based on the total volume of the ethereal medium) ether, including dihydrcarbol ether. The ethereal medium may comprise, e.g., one or more of diethyl ether, tetrahydrofuran, dioxane, dimethoxyethane, diisopropyl ether, diglyme, or methyl t-butyl ether. The ethereal medium may also comprise hydrocarbons.

In one embodiment of this invention, a process is provided for preparation of tetrakis(heptafluoronaphth-2-yl)borate salt. The process comprises; (i) combining octafluoronaphthalene and a stoichiometric excess of hydrazine in solvent below about 78° C. to form heptafluoronaphthyl hydrazine (for example, in one embodiment enough solvent is used to make a solution comprising 10 volume percent to 50 volume percent, or 20 volume percent to 40 volume percent, octafluoronaphthalene based on the total volume of the solution); (ii) combining at least a portion of the heptafluoronaphthyl hydrazine and component comprising hydrogen bromide to form bromoheptafluoronaphthalene [see, e.g., Rx (II)]; (iii) combining at least a portion of the bromoheptafluoronapthalene in ethereal medium and alkyllithium to form reaction mixture; (iv) combining boron trihalide compound and at least a portion of the reaction mixture to form lithium tetrakis (heptatluoronaphthyl)borate in the ethereal medium; (v) exchanging at least a portion of the ethereal medium with halogenated hydrocarbon; (vi) exchanging lithium cation of at least a portion of the lithium tetrakis(heptafluoronaphthyl) borate with organic cation; and (vii) precipitating tetrakis (heptafluoronaphthyl)borate salt from at least a portion of the halogenated hydrocarbon with organic cation. In certain embodiments, (i) component comprising cupric bromide is also combined with the heptafluoronaphthyl hydrazine and the component comprising hydrogen bromide; and/or (ii) the organic cation comprises N,N dimethylalinium or triphenylmethyl (Trityl). In one embodiment the solvent comprises ethanol and the temperature is between about 25° C. and about 40° C.; and/or the boron trihalide compound comprises boron trifluoride or boron trichloride; and/or the alkyllithium comprises n-butyllithium, phenyllithium, methyllithium, sec-butyllithium, or t-butyllithium.

The present invention broadly provides an improved route for the preparation of mono-hydrazine substituted ($^F$aryl) compounds, such as heptafluoronaphthyl-2-hydrazine Mono-substituted hydrazine may be prepared by combining hydrazine, including, without limitation, hydrazine hydrate, and ($^F$aryl) compound in solution at temperatures below about 78° C. In certain embodiments, in processes according to this invention, hydrazine is combined with ($^F$aryl) compound at temperatures between about 25° C. and about 78° C., or, at temperatures between about 30° C. and about 70° C., or, at temperatures between about 35° C. and about 55° C., or, at temperatures of about 40° C.

In some embodiments, in processes according to the present invention, hydrazine is combined in a stoichiometric excess with the ($^F$aryl) compound, meaning anything in excess of a stoichiometric equivalent. For example, if stoichiometrically, 1 mole of hydrazine is required per every mole of the ($^F$aryl) compound, and 10 motes of the ($^F$aryl) compound is used, then 11 motes of the hydrazine could be used (i.e., 1.1 molar equivalents of hydrazine to 1 molar equivalent of the ($^F$aryl) compound; or if 20 moles of the ($^F$aryl) compound is used, then 21 moles of the hydrazine could be used (i.e. 1.05 molar equivalents of hydrazine to 1 molar equivalent of the ($^F$aryl) compound). More than about 1.1 molar equivalents of the hydrazine to 1 molar equivalent of the ($^F$aryl) compound is considered advantageous. Typically, 3 to 5 molar equivalents of hydrazine per molar equivalent of ($^F$aryl) compound may be used; more typically molar equivalents of hydrazine of 3.5 to 4.5 per molar equivalent of ($^F$aryl) compound may be used. The amount of excess hydrazine affects the rate of conversion to monohydrazine substitution product. In one example where the molar ratio of hydrazine to ($^F$aryl) compound was 3.5, a 94% conversion was achieved in 6 hours. In another example where the molar ratio of hydrazine to ($^F$aryl) compound was about 4.5, a 96% conversion was achieved in 3.5 hours. Too much hydrazine can cause undesirable precipitation of octafluoronaphthalene and formation of di-hydrazine substituted ($^F$aryl) compounds. The upper limit of the stoichiometric excess of hydrazine used is dependent on the particular hydrazine and ($^F$aryl) compound used. The progress of the reaction may be monitored by gas chromatography. The reaction is stopped when about 95% conversion to the monohydrazine substituted product is achieved. It has been observed that at higher conversion, the yield decreases because the product is converted to bis-hydrazine. The final product may be precipitated from the organic solvent with the addition of water or may be extracted into halogenated solvents, such as chloroform, dichloromethane and the like. The final yield of the product may be determined by $^{19}$F NMR using a standard such as hexafluoro-p-xylene. In one example, the reaction was performed at 40° C. and in ethanol, which resulted in an isolated yield of greater than 76% in six hours. While ethanol is the exemplary solvent, the reaction may be conducted in other organic solvents, including but not limited to, ethylene glycol, methanol, propanol, isopropanol, acetone, tetrahydrofuran, dioxane and the like. To avoid loss of solvent due to boiling, the reaction may be conducted under pressure or reflux may be set up, as will be familiar to those skilled in the art.

Bromo($^F$aryl) compound may be prepared from mono-hydrazine substituted ($^F$aryl) compounds using the method of Brooke et al, *J. Fluorine Chem.* 1990, 50, 229 or by a modified method of Brooke as is disclosed in Mars et al, WO 99/06412, 1999, both of which references are incorporated herein as if fully set forth. Generally, the mono-hydrazine substituted ($^F$aryl) compound is treated with concentrated hydrobromic acid, and optionally copper(II) bromide, at elevated temperatures. The bromo($^F$aryl) compound may be extracted from the reaction mixture and purified by solvent exchange and crystallization. The reaction may be conducted at any suitable temperature, typically the reflux temperature of the reaction mixture. Depending on the reaction temperature, the reaction time may be between 1 to 4 hrs. The progress of the conversion may be followed by standard gas chromatography techniques. In one embodiment where 2-perfluoronaphthylhydrazine was being converted to 2-bromoheptafluoronaphthalene, the reaction was conducted at 8000 and the reaction time was about 2.5 hours. The product, 2-bromo-heptafluoronaphthalene, was extracted into methylene chloride and purified by solvent exchange into methanol and crystallized from solution by addition of water. While methylene chloride is exemplified, other halogenated solvents, such as chloroform may be used. Similarly, while methanol is exemplified as an exchange solvent, other solvents, such as ethanol, ethylene glycol, propanol, isopropanol, acetone, tetrahydrofuran, or dioxane may also be used.

The bromo($^F$aryl) compound can be converted to tetrakis($^F$aryl) borate in a single pot reaction process. Processes according to this invention comprise lithiating at least a portion of the bromo($^F$aryl) compound in ethereal medium and converting the at least a portion of the lithiated ($^F$aryl) compound into a lithium tetrakis($^F$aryl) borate salt by contacting with boron halide. The lithium tetrakis($^F$aryl)borate salt may be further converted into organic cation tetrakis($^F$aryl) borate salt by a cation exchange reaction.

The use of liquid ethereal medium/solvent appears to be beneficial for making tetrakis($^F$aryl)borate of commercially suitable purity. It has been shown that hydrocarbon solvents can be used to make the unstable lithium reagent by lithium-halogen exchange. For example, Li and Marks, *Organometallics* 1998, 17, 3996-4003 and U.S. Pat. No. 6,635,597, 2003 reports the use of lithium reagent to prepare tris(perfluoronaphtyl)borane in heptane solvent. Also, Lancaster, *Synthetic Pages* 2003, 216, reports the use of a hydrocarbon solvent for the preparation of lithium tetrakis(pentafluorophenyl)borate. However, it has been found that the reaction of heptafluoronaphthyllithium with boron trihalides in heptane produces lithium borate salt that contains significant borane and other impurities. It is further observed that when at least about half of the solvent was ether, high purity lithium tetrakis(heptafluoronaphthyl)borate was obtained. In one embodiment, the solvent is aprotic and polar, e.g., ether. Substantially pure ether solution may be used. The molar ratio of alkyllithium reagent to the bromo($^F$aryl) compound is typically close to about 1:1, and typically a slight stoichiometric excess of the bromo($^F$aryl) compound is used in the methods of the present invention (e.g., up to about 1.05 moles of the bromo($^F$aryl) compound per mole of the alkyllithium reagent). Additionally, as lithiated ($^F$aryl) compounds are known to decompose at temperatures greater than about −20° C., the lithiation reaction is generally conducted below about −20° C. Typically, the reaction is conducted at temperatures between about −20° C. and about −70° C.; alternately, the reaction is conducted between about 40° C. and about −55° C. In one embodiment, the lithiation reaction is conducted at about −50° C. The lithiation reaction is exothermic and care should be taken to avoid sudden temperature rises. To maintain the temperature, the solution containing the bromo($^F$aryl) compound may be pre-cooled to below the desired reaction temperature and the alkyllithium reagent added slowly. In one embodiment, an alkyllithium addition rate of 1 ml/min to 2 ml/min is appropriate. In one embodiment, the alkyllithium reagent is added over a period of 15 minutes or longer. In one embodiment, the solvent is more polar than a hydrocarbon and is aprotic. Generally at reaction conditions the solvent is a liquid.

Lithiated ($^F$aryl) compound and boron trihalide reagent may be combined to form lithium tetrakis($^F$aryl)borate. In one embodiment, at least four molar equivalents of lithiated ($^F$aryl) compound per molar equivalent of boron trihalide is used, in some embodiments, a slight stoichiometric excess of lithiated ($^F$aryl) compound is used (e.g., up to about 4.2 molar equivalents of lithiated ($^F$aryl) compound per molar equivalent of boron trihalide). The reaction temperature of the reaction should be maintained at below −20° C. to avoid decomposition of the lithiated ($^F$aryl) compound. The reaction of boron trihalide and the lithiated ($^F$aryl) compound is also exothermic and when the boron trihalide reagent is added to the lithiated ($^F$aryl) compound, care should be taken to add the reagent slowly while monitoring the reaction. In one embodiment, the temperature is maintained at about −45° C. The temperature of the reaction may be allow to slowly warm to about 5° C. over a time period of about 4 hours, and then allowed to stand overnight at up to about 16° C.

The organic cation tetrakis($^F$aryl)borate may be formed by contacting the lithium tetrakis($^F$aryl)borate with an organic cation salt, e.g. a protic ammonium salt, a triarylmethyl salt, or an onium salt. The protic ammonium salt can be formed shortly before reacting it with the lithium tetrakis($^F$aryl)borate; this is accomplished by reacting $R_3N$ with a protic acid to form the protic ammonium cation, wherein each R of $R_3N$ is independently a hydrocarbyl group containing up to thirty carbon atoms. Generally R is an aliphatic or aromatic hydrocarbyl group, typical hydrocarbyl groups include methyl and phenyl. Exemplary protic acids include, but are not limited to, hydrochloric acid, hydrobromic acid, hydroiodic acid, fluoboric acid, and hexafluorophosphoric acid; commonly the protic acid is hydrochloric acid. Generally, the protic ammonium cation is formed in aqueous solution. For the mixing of the protic ammonium salt and alkali metal tetrakis($^F$aryl) borate, the exclusion of water is not necessary.

Protic ammonium cations have the general formula [R$_3$NH]$^+$, wherein each R is independently a hydrocarbyl group containing up to thirty carbon atoms. Generally the R group is an aliphatic or aromatic hydrocarbyl group; typical hydrocarbyl groups include methyl and phenyl. Examples of suitable protic ammonium cations include, but are not limited to, trimethylammonium, triethylammonium, cyclohexyl(dimethyl)ammonium, tri(n-octyl)ammonium, dimethyl anilinium, diphenyl(ethyl)ammonium (diethyl anilinium), and triphenylammonium cations. As described above for the triarylmethyl salt, many inorganic anions can be appropriate counterions for the protic ammonium cation, Again, halides, especially chloride, are the most commonly used inorganic anions.

Onium cations are defined by the formula [ER$_n$]$^+$ wherein E is an element of any of Groups 15-17 of the Periodic Table, each R is independently a hydrocarbyl group containing up to thirty carbon atoms, and n is equal to the valence of E plus one. As an example of n, when E is sulfur, which has a valence of two, n is three. Typically, R is an aliphatic or aromatic hydrocarbyl group. Examples of suitable hydrocarbyl group include, but are not limited to, methyl, ethyl, isopropyl, tert-butyl, cyclopentyl, methylcyclohexyl, decyl, phenyl, tolyl, xylyl, benzyl, naphthyl, and tetrahydronaphthyl. As described previously for both the triarylmethyl salts and the protic ammonium salts, many inorganic anions may be appropriate counter-ions for the onium cation. Typically, the inorganic anions are halides, especially chloride. To form the onium tetrakis($^F$aryl)borate, standard cation exchange methods can be used. Examples of suitable onium salts include, but are not limited to, diphenyliodonium chloride, tris(p-tolyl)sulfonium bromide, and tetraethylphosphonium chloride.

For the contacting of a lithium tetrakis($^F$aryl)borate and a triarylmethyl salt, the liquid medium should be substantially dry (in the sense of having minimal water present), and typically, the reaction is conducted in an inert atmosphere comprised of one or more inert gases, such as, for example, nitrogen, helium, or argon.

Generally, the lithium($^F$aryl)borate and the organic salt, such as triarylmethyl salt, protic ammonium salt, or onium salt, are mixed together at room temperature. At least one equivalent of organic salt per equivalent of boron trihalide should be used, and typically, a 10% molar excess of organic salt is used. Some of the ion exchange reactions are exothermic and care should be taken that the temperature of the reaction mixture does not exceed the thermal decomposition temperature of the product. However, the mixture may be heated when a faster reaction rate is desired. Agitation of the reaction mixture is usually necessary for the reaction to proceed. The contact time for lithium tetrakis($^F$aryl)borate and the protic ammonium salt or onium salt is generally from about fifteen minutes to about eight hours; more typically the reaction time is in the range of from about twenty minutes to about six hours.

Theoretically, the cation exchange reaction can be conducted in any suitable liquid medium. However, it should be noted that tetrakis($^F$aryl)borate salt has a tendency of forming liquid clathrates with ether, and isolating a pure compound directly from an ethereal solvent may be difficult. The downstream isolation of the product should be considered when making the choice for the liquid medium for the ion exchange reaction.

When the organic salt is a protic ammonium salt, the ion exchange reaction may be conducted in the same ethereal medium in which the lithium tetrakis($^F$aryl) borate salt was formed, or in a liquid medium that the reaction by-products are not soluble and can be easily removed. The cation exchange reaction may be conducted in a mixture of halogenated hydrocarbon and water. The lithium tetrakis($^F$aryl)borate may be transferred to the halogenated hydrocarbon through several solvent substitutions. For example, the ethereal medium may be replaced with a hydrocarbyl medium such that the lithium tetrakis($^F$aryl)borate is precipitated in the form of a liquid clathrate. The hydrocarbyl medium may then be replaced by the halogenated hydrocarbon. The protic ammonium salt and acidified water may then be added for the exchange to occur. Suitable hydrocarbyl media include, but are not limited to pentane, hexane, heptane, octane and the like. Suitable halogenated hydrocarbons include, but are not limited to, methylene chloride, chloroform, and 1,2-dichloroethane. Alternately, the cation exchange reaction may be conducted in the same ethereal medium reaction mixture in which the lithium tetrakis($^F$aryl)borate was formed. The protic ammonium salt and acidified water may be added directly to the ethereal medium containing the lithium tetrakis($^F$aryl)borate. The pH of the aqueous phase is generally between 4-6 and typically, the pH is around 5. The reactants may be allowed to contact for a sufficient amount of time to allow the reaction to go to completion, the by-product and unreacted salts may be removed by repeated washing with water.

The final product may be isolated by precipitation when the halogenated hydrocarbon or ether is substituted by a hydrocarbyl medium in which the salt is insoluble. Alternately, the solvent substitution may be by preferential distillation of halogenated hydrocarbon or ethereal medium in the presence of the hydrocarbyl medium. When the final product is isolated from a halogenated hydrocarbon, the hydrocarbyl medium may be any hydrocarbon, e.g., heptane, ISOPAR™ E, which has a higher boiling point than the halogenated hydrocarbon. However, to effect sufficient removal of the ethereal solvent, it is desirable that the boiling point of the hydrocarbyl medium is significantly higher than the boiling point of the ethereal medium. Typically, the difference in the two boiling temperatures is greater than 100° C.; more typically, the difference in boiling temperature is about 80° C. Exemplary solvents that may be used with diethyl ether, include but are not limited to, octane, nonane, decane and the ISOPAR™ fluids (high-purity, synthetic, hydrocarbon fluids sold by ExxonMobil Chemical) such as ISOPAR™ E (initial boiling point at about 115° C.).}

The substituting of the liquid in which the lithium tetrakis($^F$aryl)borate is dissolved or slurried with another liquid can be accomplished by a variety of means. Typical methods include decantation, solvent exchange via distillation (not to dryness), gentle evaporation (not to dryness), and centrifugation. If the two media are immiscible, they can be allowed to separate and one decanted. The key is that the lithium tetrakis($^F$aryl)borate is not isolated from solvent at any point during the substitution.

The following examples are presented for purposes of illustration, and are not intended to impose limitations on the scope of this invention.

EXAMPLES

Example 1

Preparation of Perfluoronaphthyl-2-hydrazine

Octafluoronaphthatene (OFN) (55.4 g, 0.204 mol) was dissolved in absolute EtOH (202 g) at 40° C. Hydrazine hydrate, 85% (43 g, 0.73 mol) was added over a period of 30 minutes.

The OFN precipitated during the addition and re-dissolved as it reacted. The reaction progress was monitored by GC, and after 6 hr. a 94% conversion to the monohydrazine substitution product was observed. The reaction mixture was cooled to ambient temperature, and then 240 g of water was added. The product precipitated as a fine solid, which was filtered, washed with 200 g of 50% ethanol water and dried in vacuum for 10 hr. The product was a yellow solid (60.0 g) which assayed 73.5% by standard NMR analysis. The yield was 76%.

Example 2

Octafluoronaphthalene to heptafluoronaphthyl-2-hydrazine

A jacketed glass reactor was charged with 568 g of ethanol and 168 g of octafluoronaphthalene (Lancaster, 97%) (163 g contained 0.599 mol). The solution was stirred at 40° C. while adding 155 ml (160 g) of 85% hydrazine hydrate (136 g neat basis, 2.72 mol) over 37 min, and keeping the temperature within the range of 40° C. to 4200. After 3.5 hours, a GC analysis of a sample showed 96% conversion to product. After the mixture was cooled to 19° C., 250 g of water was added which raised the temperature to 28° C. Then 1.5 kg of methylene chloride and 650 g of water were added. The mixture was agitated, settled, and the layers separated. The aqueous layer was extracted with 130 g of methylene chloride, and then the combined organic phases were washed with 1 kg of water. $^{19}$F NMR analysis of the organic phase using hexafluoro-p-xylene as internal standard showed that the 1783 g of product solution was 8.5 wt % naphthylhydrazine (0.534 moles), an 89% yield.

Example 3

Conversion of heptafluoronaphthyl-2-hydrazine to 2-bromoheptafluoronaphthalene

A glass reactor equipped with a paddle-stirrer, a thermometer, and a distillation head was charged with 781 g of 48% HBr, and 292 g of $CuBr_2$; the mixture was heated to 45° C. with the heating jacket set at 50° C. 886 g (66.5 g neat basis) of the methylene chloride solution of heptafluoronaphthyl-2-hydrazine prepared in example 2 above was added to the mixture over a 90 mm period. During this time, the methylene chloride was continually being distilled off and collected. After the addition was completed, the addition funnel was rinsed with 50 ml of methylene chloride and the rinse was added to the mixture. The temperature of the reaction mixture was raised to 80° C. After 2.5 h, analysis of a sample of the reaction mixture by GC showed complete conversion of the heptafluoronaphthyl-2-hydrazine. The reaction mixture was cooled to 19° C. 825 g of water was added; the mixing in of water was exothermic and the temperature of the reaction mixture increased to 29° C. The reaction mixture was cooled back to 19° C. The methylene chloride distillate (617 g) collected was returned to the flask. This batch of product was combined with another batch of product made from 76 g of heptafluoronaphthyl-2-hydrazine (total 143 g, 0.503 mol) and 15 g of crude 2-bromoheptafluoronaphthalene of about 75% purity for the following work-up steps.

The combined methylene chloride solution containing the crude product was washed with 750 g of water, and then the organic phase (1428 g) was distilled to remove methylene chloride, replacing it with methanol. A total of 1432 g of distillate was collected, and a total of 1024 g of methanol was added. After the distillation, 5.4 g of decolorizing carbon was added to the hot methanol solution, and the hot solution was filtered through 4 g of Celite. The cake was washed with 105 g of methanol. About 1.00 kg of filtrate was collected. The mixture was cooled to 31° C.; while stirring, 160 g of water was added and the product precipitated out. The reaction mixture was allowed to stand overnight, then stirred and filtered. The solid was washed with 261 g of 72% methanol/water and dried in a vacuum for 20 h to give 138 g of product with about 90% purity. For the purpose of yield calculation, of the 138 g of product, about 10 g was assumed to be from the 15 g of crude 2-bromoheptafluoronaphthalene added. After subtracting this amount, the yield was calculated at 64%.

Example 4

Preparation of Lithium Naphtylborate Dimethylanilinium tetrakis(perfluoronaphth-2yl)borate A flask was charged with 70.4 g (0.211 mol) of heptafluoro-2-bromonaphthalene and 519 g of ether. This solution was cooled to −50° C. and then 93 ml 2.3 M n-BuLi in hexanes (0.214 mol) was added. The temperature was −50° C. to −44° C. during the 42 min addition period. The addition funnel was rinsed with 8 g of heptane, and then charged with 48 ml of 1.09 M $BCl_3$ in heptane solution (52.3 mmol). The addition took 17 min and the temperature was maintained at about 45° C. to −43° C. After the addition was completed, the reaction mixture was allowed to warm to 5° C. over 4 h, and then allowed to stand overnight at up to 16° C. Then, 203 g of solvents were distilled off at atmospheric pressure and replaced with 480 g of heptane. Additional solvents (308 g) were stripped at a pot temperature of 79° C. and a head temperature of 68° C. More heptane (48 g) was added and the mixture was cooled to 30° C. The mixture then contained a clear upper phase of mostly heptane with residual ether, bromobutane, and some fluorinated aromatics, but no lithium naphthylborate. The upper phase was decanted (591 g). The lower, viscous phase contained the product, a liquid clathrate of lithium tetrakisperfluoronaphthylborate, and the by-product, LiCl, suspended in it.

Example 5

Preparation of Dimethylanilinium tetrakis(perfluoronaphth-2-yl)borate

Lithium tetrakisfluoronaphthylborate remaining in the bottom phase in Example 4 above was used to prepare dimethyanilinium tetrakis(heptafluoronaphth-2-yl)borate. About 665 g of methylene chloride was added to the bottom phase and the mixture was stirred to give a slurry. At ambient temperature, 213 g of 1.00% HCl (58.2 mmol) was added, dissolving the solid and giving two liquid phases. To this was added 7.04 g of N,N-dimethylaniline (57.9 mmol), and the two-phase mixture was stirred for 2 h. The pH of the aqueous phase was 5. The phases were separated and the organic phase was washed with 200 g of distilled water. For isolating the product, a 2 L flask was set up for distillation and charged with 823 g of heptane, the heptane was heated to boiling. When the distillation just started, the methylene chloride solution containing the product, dimethyanilinium tetrakis(heptafluoronaphth-2-yl)borate, was fed dropwise from an addition funnel into the boiling heptane. During the feed, 604 g of heptane was added to the pot to maintain the liquid level. A total of 1,396 g of distillate was collected. All of the solid product had caked on the walls, (Better results were obtained in other preparations by using a subsurface feed). After cooling, the product was scraped off with a spatula, filtered, and washed with hexanes. After drying in a vacuum at ambient temperature, the product was ground in a mortar, and then dried for 16 h at 130° C. in a vacuum, Nitrogen was admitted occasionally to help with water removal. The product, 52.6 g, 45.9 mmol (87% yield based on bromoheptafluoronaphthalene) was very hygroscopic and found to contain 1100 ppm water.

Example 6

Preparation of Dimethylanilinium tetrakis(perfluoronaphth-2-yl)borate

A sample of 2-bromoheptafluoronaphthalene (31.1 g, 93.5 mmol) was dissolved in 257 g of ether. This was cooled to −54° C. and then 42 mL of 2.3 M BuLi in hexanes was added over a 36 min period. The temperature rose to −48° C. during the addition. The solution was warmed to 43° C., and a solution of boron trichloride in heptane (0.9 M, 25 mL, 22.5 mmol) was added while the temperature was maintained at below −40° C. After the addition, the solution was allowed to warm to −35° C. and kept at that temperature while the reaction was occurring. After 30 minutes, the solution was warmed to 10° C. over a 2-h period. Heptane (146 g) was added and the mixture was heated to boiling and distilled at atmospheric pressure to remove 178 g of distillate. During the distillation, 91 g of heptane was charged to maintain the liquid level. The mixture was allowed to cool to ambient temperature. A viscous liquid phase separated at the bottom of the flask, and the upper layer (75% heptane, 22% ether, 3% butylbromide) was decanted off.

To the bottom phase was added 251 g of methylene chloride, and 95 g of 0.94% HCl. The solids dissolved giving two liquid phases. Next was added N,N-dimethylaniline (3.01 g) and the mixture was stirred for 2 hr. The aqueous phase was separated and decanted and the organic phase was washed with 100 g of water. Another flask charged with 414 g of heptane was set Lip for simple distillation. While the liquids in the flask was boiling, the methylene chloride solution which contained the product was fed dropwise over 1.5 h, the pot temperature dropped to as low as 7900+A brown solid deposited during the feed. The distillation continued after the feed was finished until the port temperature reached 92° C. An additional 201 g of heptane was fed to keep the volume in the pot near constant. A total distillate of 564 g was collected. The flask was cooled to ambient, and the solids were filtered off, Washing with 216 g of hexanes, drying at 121° C. under a nitrogen stream for 5.5 hr., gave 21.2 g of N,N-dimethylanilinium tetrakis(perfluoronaphth-2-yl)borate (79% yield based on bromoheptafluoronaphthalene).

Example 7

Counterexample Run in Heptane

A sample of 2-bromoheptafluoronaphthalene (5.91 g, 17.7 mmol) was dissolved in 95 g of heptane and then the solution was cooled to −45° C. The solute precipitated on cooling. To this slurry was added 7.8 ml of 2.3 M n-BuLi in hexanes (17.9 mmol). The slurry was stirred at −40° C. to −35° C. for 1 h after the addition was complete. Then, while the slurry was at −35° C., 4.2 ml of 1 M BCl$_3$ (4.2 mmol) in heptane solution was added. The mixture was kept at −40 to 45° C. for 40 min after the addition, and then slowly warmed to 0° C. over 1.5 h, and then to ambient temperature after 3 h. The reaction mixture was suction filtered and the solid was washed with 40 g of heptane. Drying in a vacuum gave 6.18 g of yellow solid. The $^{19}$F NMR spectrum in d$_8$-THF exhibited 14 multiplets, indicating that the product was impure.

Example 8

Process without a Heptane Solvent Swap

A flask is charged with 70.4 g (0.211 mol) of heptafluoro-2-bromonaphthalene and 519 g of ether. This solution is cooled to −50° C. and then 93 ml of 2.3 M n-BuLi in hexanes (0.214 mol) is added. The temperature is maintained at −5° C. to −44° C. during the 42 min addition period. The addition funnel is rinsed with 8 g of heptane, and then charged with 48 ml of 1.09 M BCl$_3$ in heptane solution (52.3 mmol). The addition takes 17 min and is carried out at a temperature range of −45° C. to −43° C. After the addition is complete, the reaction mixture is allowed to warm to 5° C. over 4 h, and then allowed to stand overnight at up to 16° C. The reaction mixture is washed with 200 g of water. Then to the organic phase 213 g of 1.00% HCl (58.2 mmol) and 7.04 g N,N-dimethylaniline (57.9 mmol) are added, and the two-phase mixture is stirred 2 h. The phases are separated and the organic phase is washed with 200 g of distilled water. For the product isolation, a 2 L flask was set up for distillation and charged with 823 g of ISOPAR® E and heated to distill. When the distillation starts, the ether solution of dimethylanilinium tetris (heptafluoronaphth-2-yl)borate is fed slowly below the surface of the boiling ISOPAR® E. At the same time, ISOPAR® E is added to maintain the liquid volume fairly constant. The product precipitates during the feed. When the feed is completed, an additional 1 kg of ISOPAR® E is distilled off to ensure ether and water removal. The product slurry is cooled to ambient temperature, filtered, and washed with hexanes. Residual solvent is removed from the product by drying in a vacuum or a nitrogen stream at about 80° C.

It is to be understood that the reactants and components referred to by chemical name or formula anywhere in the specification or claims hereof whether referred to in the singular or plural, are identified as they exist prior to coming into contact with another substance referred to by chemical name or chemical type (e.g., another reactant, or a solvent, etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

While the present invention has been described in terms of one or more preferred embodiments, it is to be understood that other modifications may be made without departing from the scope of the invention, which is set forth in the claims below.

GLOSSARY OF TERMS

As used herein, the term the term "$^F$aryl" or "($^F$aryl)" means a fluorine-containing aryl group that has bonded to an aromatic ring at least two fluorine atoms, or at least two perfluorohydrocarbyl groups, or at least one fluorine atom and at least one perfluorohydrocarbyl group. Typically, at least two fluorine atoms or at least two perfluorohydrocarbyl groups are bonded to the aromatic ring. Exemplary aromatic rings include, but are not limited to, benzene, naphthalene, anthracene, biphenyl, phenanthrene, or indene. Suitable perfluorohydrocarbyl groups include, but are not limited to, trifluoromethyl, pentafluoroethyl, pentafluorophenyl, and heptafluoronaphthyl.

As used herein the term "alkyl," alone or in combination, refers to an optionally substituted straight-chain, optionally substituted branched-chain, or optionally substituted cyclic alkyl radical having from 1 to about 30 carbons, typically 1 to 12 carbons. Examples of alkyl radicals include, but are not limited to, methyl, ethyl, n-propyl, isopropyl, n-butyl, isobutyl, sec-butyl, ter-butyl, tert-amyl, pentyl, hexyl, heptyl, octyl and the like.

As used herein, the term "alkyllithium" refers to a reagent composed of an alkyl group as described above and a lithium atom. Exemplary alkyllithiums include, but are not limited to, n-butyllithium, phenyllithium, methyllithium, sec-butyllithium, and t-butyllithium.

As used herein, term "ethereal medium" comprises at least about 50% by volume (based on the total volume of the ethereal medium) ether, including dihydrocarbol ether. The ethereal medium may comprise, e.g., one or more of diethyl ether, tetrahydrofuran, dioxane) dimethoxyethane, diisopropyl ether, diglyme, or methyl t-butyl ether. The ethereal medium may also comprise hydrocarbons.

The term "optionally" denotes that the step or component following the term may, but need not be, a part of the method or the formulation.

What is claimed is:

1. A process comprising:
   (i) combining brominated ($^F$aryl) compound and alkyllithium in the presence of first solvent comprising a hydrocarbon or an ether to produce a first product;
   (ii) combining at least a portion of the first product and boron trihalide in the presence of an solvent comprising ether to produce a second product; and
   (iii) isolating tetrakis($^F$aryl) borate salt from the second product.

2. The process of claim 1 wherein the tetrakis($^F$aryl) borate salt comprises tetrakis(perfluoronaphthyl)borate; tetrakis(perfluoronaphth-2-yl)borate; lithium tetrakis(perfluoronaphthyl)borate, and/or lithium tetrakis(perfluoronaphth-2-yl)borate.

3. The process of claim 1 wherein the brominated($^F$aryl) compound comprises 2-bromoheptafluoronaphthalene.

4. The process of claim 1 wherein the alkyllithium comprises butyllithium.

5. The process of claim 1 wherein the boron trihalide comprises boron trichloride.

6. The process of claim 1 wherein (iii) comprises combining at least a portion of the second product and second solvent.

7. The process of claim 6 wherein the second solvent comprises halogenated hydrocarbon.

8. A process comprising:
   (i) combining ($^F$aryl) compound and hydrazine in solvent below about 78° C. to form ($^F$aryl);
   (ii) converting at least a portion of the ($^F$aryl) hydrazine to bromo($^F$aryl) compound;
   (iii) combining at least a portion of the bromo($^F$aryl) compound and alkyllithium in a hydrocarbon or ethereal medium to form a reaction mixture;
   (iv) combining boron trihalide compound and at least a portion of the reaction mixture in the presence of an ethereal medium to form lithium tetrakis($^F$aryl)borate; and
   (v) exchanging lithium cation from at least a portion of the lithium tetrakis($^F$aryl)borate for cation of organic salt to form tetrakis($^F$aryl)borate salt.

9. The process of claim 8 wherein the ethereal medium comprises at least about 50% by volume of ether.

10. The process of claim 8 wherein the boron trihalide compound comprises boron trifluoride and/or boron trichloride.

11. The process of claim 8 wherein the alkyllithium comprises n-butyllithium, phenyllithium, methyllithium, sec-butyllithium, t-butyllithium, or hexyllithium.

12. The process of claim 8 wherein the organic salt comprises triarylmethyl salts, protic ammonium salts, or onium salts.

13. The process of claim 9 wherein the ether comprises one or more of diethyl ether, tetrahydrofuran, dioxane, dimethoxyethane, diisopropyl ether, diglyme, or methyl t-butyl ether.

14. A process comprising:
   (i) combining octafluoronaphthalene and a stoichiometric excess of hydrazine in solvent below about 78° C. to form heptafluoronaphthyl hydrazine;
   (ii) combining at least a portion of the heptafluoronaphthyl hydrazine and component comprising hydrogen bromide to form bromoheptafluoronaphthalene;
   (iii) combining at least a portion of the bromoheptafluoronapthalene in a hydrocarbon or ethereal medium and alkyllithium to form a reaction mixture;
   (iv) combining boron trihalide compound and at least a portion of the reaction mixture in an ethereal medium to form lithium tetrakis(heptafluoronaphthyl)borate in the ethereal medium;
   (v) exchanging at least a portion of the ethereal medium with halogenated hydrocarbon;
   (vi) exchanging lithium cation of at least a portion of the lithium tetrakis(heptafluoronaphthyl)borate with organic cation; and
   (vii) precipitating tetrakis(heptafluoronaphthyl)borate salt from at least a portion of the halogenated hydrocarbon with organic cation.

15. The process of claim 14 wherein at least a portion of the solvent comprises ethanol and the temperature is between about 25° C. and about 40° C.

16. The process of claim 14 wherein the boron trihalide compound comprises boron trifluoride or boron trichloride.

17. The process of claim 14, wherein the alkyllithium comprises n-butyllithium, phenyllithium, methyllithium, sec-butyllithium, or t-butyllithium.

18. The process of claim 14 wherein step (ii) is replaced with: (ii) combining (a) at least a portion of the heptafluoronaphthyl hydrazine and (b) component comprising hydrogen bromide and cupric bromide to form bromoheptafluoronaphthalene.

* * * * *

UNITED STATES PATENT AND TRADEMARK OFFICE
CERTIFICATE OF CORRECTION

PATENT NO. : 8,642,497 B2  Page 1 of 1
APPLICATION NO. : 12/097246
DATED : February 4, 2014
INVENTOR(S) : Bruce C. Berris It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this

Twenty-ninth Day of September, 2015

Michelle K. Lee
*Director of the United States Patent and Trademark Office*